United States Patent
Lieber et al.

(10) Patent No.: US 10,119,955 B2
(45) Date of Patent: Nov. 6, 2018

(54) HIGH-RESOLUTION MOLECULAR SENSOR

(71) Applicant: President and Fellows of Harvard College, Cambridge, MA (US)

(72) Inventors: Charles M. Lieber, Lexington, MA (US); Qihua Xiong, Singapore (SG); Ping Xie, Needham, MA (US); Ying Fang, Beijing (CN)

(73) Assignee: President and Fellows of Harvard College, Cambridge, MA (US)

( * ) Notice: Subject to any disclaimer, the term of this patent is extended or adjusted under 35 U.S.C. 154(b) by 969 days.

(21) Appl. No.: 14/186,056

(22) Filed: Feb. 21, 2014

(65) Prior Publication Data
US 2014/0166487 A1    Jun. 19, 2014

Related U.S. Application Data

(62) Division of application No. 12/677,573, filed as application No. PCT/US2008/010637 on Sep. 12, 2008, now Pat. No. 8,698,481.

(Continued)

(51) Int. Cl.
*G01N 33/487* (2006.01)
(52) U.S. Cl.
CPC .............................. *G01N 33/48721* (2013.01)
(58) Field of Classification Search
CPC .................................................. G01N 27/4473
See application file for complete search history.

(56) References Cited

U.S. PATENT DOCUMENTS 6,413,792 B1 * 7/2002 Sauer et al. ...... B01L 3/502761
257/253
6,627,067 B1 * 9/2003 Branton et al. ....... B24B 37/013
204/403.06

(Continued)

FOREIGN PATENT DOCUMENTS

EP    1441213 A1    7/2004
EP    1486775       12/2004

(Continued)

OTHER PUBLICATIONS

PCT/US2008/010637, International Search Report, PCT/ISA/210 first sheet, second sheet pp. 1-2, and patent family annex, dated Dec. 2008.

(Continued)

*Primary Examiner* — Gautam Prakash
(74) *Attorney, Agent, or Firm* — Theresa A. Lober

(57) ABSTRACT

A solid state molecular sensor having an aperture extending through a thickness of a sensing material is configured with a continuous electrically-conducting path extending in the sensing material around the aperture. A supply reservoir is connected to provide a molecular species, having a molecular length, from the supply reservoir to an input port of the aperture. A collection reservoir is connected to collect the molecular species from an output port of the aperture after translocation of the molecular species from the supply reservoir through the sensing aperture. The sensing aperture has a length between the input and output ports, in the sensing material, that is substantially no greater than the molecular length of the molecular species from the supply reservoir. An electrical connection to the sensing material measures a change in an electrical characteristic of the sensing material during the molecular species translocation through the aperture.

20 Claims, 4 Drawing Sheets

Related U.S. Application Data

(60) Provisional application No. 60/993,388, filed on Sep. 12, 2007.

(56) References Cited

U.S. PATENT DOCUMENTS

| | | | |
|---|---|---|---|
| 7,468,271 B2* | 12/2008 | Golovchenko et al. | ............... C12Q 1/6869 435/287.2 |
| 7,803,607 B2 | 9/2010 | Branton et al. | |
| 8,092,697 B2 | 1/2012 | Branton et al. | |
| 2002/0117659 A1 | 8/2002 | Lieber et al. | |
| 2004/0229386 A1* | 11/2004 | Golovchenko et al. | ............... G01N 33/48721 438/10 |
| 2005/0019784 A1 | 1/2005 | Su et al. | |
| 2006/0063171 A1* | 3/2006 | Akeson et al. | ... B01L 3/502707 435/6.11 |
| 2006/0207880 A1* | 9/2006 | Joyce et al. | ...... B01L 3/502746 204/451 |
| 2006/0275778 A1 | 12/2006 | Wu et al. | |
| 2006/0275779 A1 | 12/2006 | Li et al. | |
| 2006/0275911 A1 | 12/2006 | Wang et al. | |
| 2007/0092432 A1 | 4/2007 | Prud'Homme et al. | |
| 2007/0178507 A1* | 8/2007 | Wu et al. | ............. C12Q 1/6825 435/6.12 |
| 2007/0187694 A1 | 8/2007 | Pfeiffer et al. | |
| 2011/0089404 A1 | 4/2011 | Marcus et al. | |
| 2011/0155574 A1 | 6/2011 | Golovchenko et al. | |
| 2012/0234679 A1 | 9/2012 | Garaj et al. | |

FOREIGN PATENT DOCUMENTS

| | | |
|---|---|---|
| WO | 200181908 | 11/2001 |
| WO | 2007084163 | 7/2007 |
| WO | 2012138357 | 10/2012 |

OTHER PUBLICATIONS

PCT/US2008/010637, Written Opinion of the International Searching Authority, PCT/ISA/237 cover sheet: pp. 1-3, and Separate sheet: sheets 1-6, dated Dec. 2008.

European Patent Application No. 08830263.3, EP Examiner Communication, pp. 1-2, dated May 2010.

European Patent Application No. 08830263.3, Response to EP Examiner Communication: pp. 1-4, amendments: pp. 1-3, dated Jun. 2010.

PCT/US2010/049238, International Search Report, PCT/ISA/220 sheet 1, PCT/ISA/210 first sheet, second sheet pp. 1-2, and patent family annex, and Written Opinion of the International Searching Authority, PCT/ISA/237 cover sheet: pp. 1-3, and Separate sheet: sheets 1-4, dated Jan. 2011.

PCT/US2011/034426, International Search Report, PCT/ISA/210 first sheet, second sheet pp. 1-2, and patent family annex, dated Oct. 2011.

Xie, "Silicon nanowires: Fundamental Properties and Application in DNA Sequencing," Ph.D. Thesis Dissertation, Harvard University, Department of Chemistry and Chemical Biology, Cambridge MA, pp. 1-126, May 2008.

Novoselov et al., "Electric field effect in atomically thin carbon films," Science, vol. 306, No. 5696, pp. 666-669, Oct. 2011.

Schedin et al., Detection of individual gas molelcules adsorbed on graphene, Nature, vol. 6, No. 9, pp. 652-655, Sep. 2007.

PCT/US2009/041488, International Search Report, PCT/ISA/210 first sheet, second sheet, and patent family annex, dated Dec. 2009.

PCT/US2009/041488, International Preliminary Report on Patentability, PCT/IB/373, PCT/ISA/237 cover sheet, Box No. I sheet, Box No. V sheet, Supplemental Box sheet, dated Oct. 2010.

Wang et al., "Label-free detection of small-molecule-protein interactions by using nanowire nanosensors," PNAS, vol. 102, No. 9, pp. 3208-3212, Mar. 2005.

Hahm et al., "Direct Ultrasensitive Electrical Detection of DNA and DNA Sequence Variations Using Nanowire Nanosensors," Nano Letters, vol. 4, No. 1, pp. 51-54, Dec. 2003.

Li et al., "Ion-beam sculpting at nanometre length scales," Nature, vol. 412, pp. 166-169, Jul. 2001.

Lieber et al., "Functional Nanowires," MRS Bulletin, vol. 32, pp. 99-108, Feb. 2007.

Desai et al., "Nanopore Technology for Biomedical Applications," Biomedical Microdevices, 2:1, pp. 11-40, 1999.

Geim et al., "The rise of graphene," nature materials, vol. 6, pp. 183-191, 2007.

* cited by examiner

United States Patent US 10,119,955 B2

HIGH-RESOLUTION MOLECULAR SENSOR

CROSS-REFERENCE TO RELATED APPLICATIONS

This application is a divisional of U.S. application Ser. No. 12/677,573, filed Jun. 28, 2010, now issued as U.S. Pat. No. 8,698,481, the entirety of which is hereby incorporated by reference. U.S. application Ser. No. 12/677,573, in turn is a national stage application under 35 U.S.C. § 371 of International Application No. PCT/US08/10637, filed Sep. 12, 2008, which claims the benefit of U.S. Provisional Application No. 60/993,388, filed Sep. 12, 2007, the entirety of all of which are hereby incorporated by reference.

STATEMENT REGARDING FEDERALLY SPONSORED RESEARCH

This invention was made with Government support under Contract No. FA8650-06-C-7622, and No. FA8560-06-C-7618, awarded by DARPA. The Government has certain rights in the invention.

BACKGROUND OF INVENTION

This invention relates generally to nanoscale devices, and more particularly relates to nanoscale devices for detecting and analyzing species such as molecules components of molecules.

The detection, analysis, and quantification of biological and chemical species, such as DNA, has become the central focus of a wide range of applications for areas of healthcare and the life sciences, ranging from diagnosis of disease to discovery and screening of new drug molecules. Of particular interest is an ability to carry out single molecule sensing. The ability to study a biological system one molecule at a time enables observation of, e.g., time trajectories and characterization of biological pathways, offering fundamental insight into biophysical problems.

There have been proposed a wide range of nanopore-based structures for molecular sensing. Nanopores are generally considered to be apertures having a diameter on the nanoscale. It has been suggested to translocate a strand of DNA through a solid-state nanometer-diameter pore provided in an ionic solution to measure the blockage of ionic current through the nanopore during the DNA translocation. But the small ionic current differences resulting from the translocation of different DNA bases are generally beyond the resolution limit of conventional current amplifiers because the intrinsic noise due to the charged DNA bases is so large, and it is therefore not possible to discriminate between specific bases. To overcome this low signal-to-noise ratio, it has been proposed to alternatively employ an electronic sensing arrangement, or electronic sensor, such as a tunneling junction, at the site of a nanopore, for sensing molecules translocating through the nanopore. While such configurations are expected to provide an improved signal-to-noise ratio, they cannot, in general, achieve single nucleotide sensitivity.

SUMMARY OF THE INVENTION

Herein is provided a molecular sensing device having the requisite configuration to enable single molecule resolution, overcoming the limitations of prior molecular sensors. In the molecular sensor device there is provided a solid state and electrically conducting sensing material that includes a sensing aperture extending through a thickness of the sensing material. A continuous, electrically conducting path extends in the sensing material around the sensing aperture. A supply reservoir is connected to provide a molecular species, having a molecular length, from the supply reservoir to an input port of the sensing aperture. A collection reservoir is connected to collect the molecular species at an output port of the sensing aperture, after translocation of the molecular species from the supply reservoir through the sensing aperture. The sensing aperture has length between the input port and the output port, in the sensing material, that is substantially no greater than the molecular length of the molecular species from the supply reservoir. An electrical connection to the sensing material is provided to measure a change in an electrical characteristic of the sensing material during the molecular species translocation through the sensing aperture.

This molecular sensing device is particular advantageous for detection of biomolecules, such as DNA and RNA, as well as for distinction between nucleic acid bases. Other features and advantages of the invention will be apparent from the following description and accompanying figures, and from the claims.

DETAILED DESCRIPTION OF THE INVENTION

Figure 1:
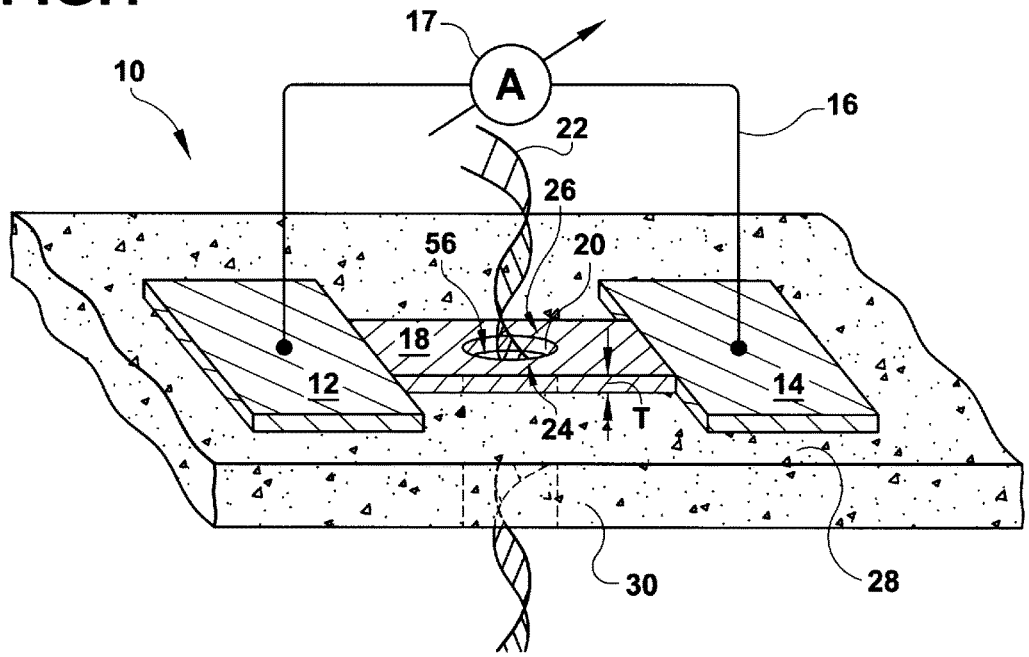
FIG. 1 is a perspective schematic view of an example molecular sensor of the invention.

Referring to FIG. 1, there is schematically represented an example implementation of the nanoscale sensor 10 of the invention. In this example, there is provided a field-effect transistor (FET) configuration in which an electrically conducting source region 12 and an electrically conducting drain region 14 are connected in a sensing circuit 16. Electrical current is injected and collected between the source and drain through a molecular sensing channel region 18. The molecular sensing channel region includes an aperture 20, preferably a nanopore, that is disposed centrally, at an edge of, or just adjacent to, the channel region. In the example of FIG. 1, the nanopore aperture is provided generally centrally to the channel region 18. Other aperture arrangements are described below. The channel region and source and drain regions are provided on a support structure 28 having an aperture 30 through the thickness thereof that is in communication with the nanopore 20 of the channel region for translocating species such as molecules completely through the channel region and the support structure.

In a conventional FET arrangement, a semiconducting channel region such as a p-type silicon region is connected between source and drain regions through which current is injected and collected. The conductance of the conventional FET device is controlled by the external application of a voltage to a gate electrode that is typically capacitively coupled to the channel region through a dielectric layer. In the sensing device 10 of the invention, no such gate is provided. Instead, the sensor 10 is provided in an environment in which analyte species, such as molecules, e.g., strands of DNA 22, can be translocated through the nanopore 20 in the channel region 18. As a molecule translocates through the nanopore 20 of the channel region, the electric field in the vicinity of the nanopore is modified by the electric charge that is particular to that molecule. This change in electric field caused by a translocating molecule is analogous to the application of a voltage to the channel region using a gate electrode.

The channel region 18 includes at least one electrically conductive path, around or adjacent to the nanopore, between the source and drain regions 12, 14. In other words, the nanopore does not extend through the complete width of the channel region. At least one portion of the channel region is continuous along the length of the channel region to form a complete circuit with the source and drain regions. In the example of FIG. 1, two channel portions 24, 26, each adjacent to the nanopore 20, are continuous along the length of the channel region between the source and drain regions. Electrical conduction, of holes or electrons, through the channel region is therefore continuous as molecules translocate through the nanopore.

With this arrangement, the translocation of a molecule or other species through the nanopore modulates the conductance of the channel region by modifying the electric field at the nanopore, i.e., the translocation event adjusts the flow of holes or electrons through the continuous portions of the channel between the source and drain regions. This conductance modulation results in a direct change in circuit parameters and the ability to directly detect the translocation event.

Figure 2A:
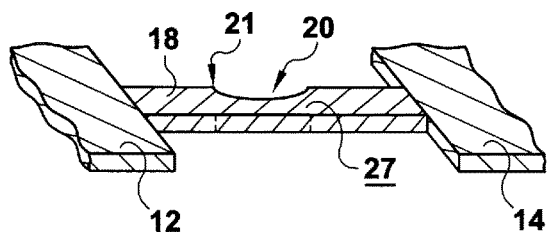
FIGS. 2A-2C are perspective schematic views of three example nanopore configurations provided by the invention for the molecular sensor of FIG. 1.
Figure 2B:
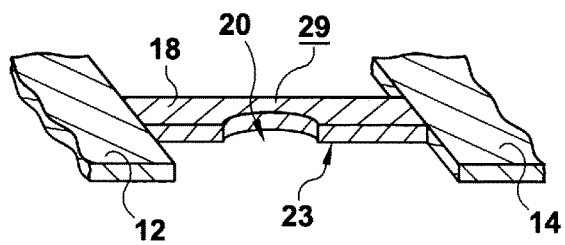
Figure 2C:
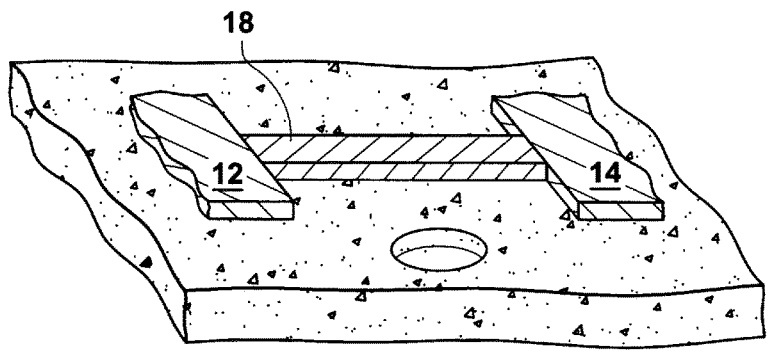

Other alternative example arrangements for the nanopore are shown schematically in FIGS. 2A-2C. The nanopore 20 can be disposed at an edge 21, 23, of the channel region, as shown in FIGS. 2A-2B, where the nanopore cuts into only a side of the channel region, maintaining a continuous portion 27, 29, respectively, at the opposite channel region side. Alternatively, the nanopore 20 can be provided adjacent to the channel region 18 in the support structure 28.

In all of the nanopore arrangements of FIGS. 1-2, the nanopore guides translocation of an analyte through or directly adjacent to the channel region. Whether the nanopore is in the channel region or adjacent to the channel region, as the translocation of an analyte, such as a molecule, through the nanopore proceeds, the electric field local to the channel region is altered. This change in electric field results in a corresponding change in conductance of the channel region and a change in electrical current conducted between the source and drain in the sensing circuit, as explained above.

The nanopore aperture arrangements of FIGS. 1-2 are not meant to imply a particular aperture diameter. In accordance with the invention, the hole that is provided in the channel region or adjacent to the channel region can be characterized as a pore, a channel, an aperture, or other opening that extends from one side of the channel region to the other, e.g., from the top of the channel region layer to the bottom of the channel region layer. As explained below, the extent of the hole, i.e., the hole diameter, can be selected based on a species to be analyzed, such that the extent corresponds in some fashion to the species. A nanopore aperture is an aperture having a diameter that is less than 1 μm. Other aperture diameters can be suitable. The geometric shape of the aperture opening can also be tailored to suit a selected application. A generally circular, or square, angled, or other geometry can be selected. No particular geometry is required. For ease of clarity, and with regard to specific examples, the aperture is generally referred to herein as a nanopore, given the microscale nature of FET devices in general, but it is to be recognized that the nano-scale of such is not a universal requirement for the aperture.

Whatever the selected aperture configuration and geometry, in accordance with the invention, a selected circuit parameter, such as current or capacitance, is monitored to carry out molecule-specific sensing as molecules translocate through the aperture, e.g., a nanopore. The FET circuit 16, as in FIG. 1, includes one or more circuit detection devices 17 or systems for detecting a change in one or more circuit parameters during a translocation event. An ammeter, or other measuring device or computer system can be used as-suited for a given application. The measured circuit parameter corresponds to an electrical characteristic of the channel region; e.g., a change in circuit current corresponds to a change in channel region conductance.

The channel region is provided as a selected solid state material disposed on the support structure in a geometry selected for the FET operation. The channel region can be a layer, a strip, or other general expanse, and can be patterned in a specific geometry or provided in a general form. No particular channel region geometry is required except that a continuous connection between the source and drain regions be provided and that the channel region be provided as a solid state structure.

In accordance with the invention, in one embodiment, high-resolution sensing of distinct translocation events is enabled by providing the channel region 18 as a material having a thickness that is in general on the order of, no greater than, or less than the extent of a particular molecular species to be sensed. Specifically, the thickness, T, of the channel region, as shown in FIG. 1, is here preferably set to correspond to the number of distinct entities, such as molecules or at least molecular components, desired to be translocating through the nanopore together at a given time. In one example implementation, the thickness of the channel region, and the corresponding nanopore extent through that thickness, is selected to be on the order of, and more preferably no greater than, the general extent of a single molecule or a molecular component to be detected during translocation through the nanopore. With this configuration, one or only a few molecules or molecular components are present in the nanopore extending through the thickness of the channel region at a given time. As a result, changes in the conductance of the channel region during a given translocation event can be attributed specifically to a single or only a few molecules or molecular components rather than a large number of such.

The nanopore "length," or "span," through the thickness of the channel region material is herein meant to refer to the linear extent of the nanopore from an input port at a first planar surface of the channel region material to an output port at an opposite, second surface of the channel region material. The channel region material alone is considered in determining the extent of the nanopore through the channel region. The nanopore provided in the support structure below the channel region material is not considered in this analysis because in general, as explained below, the support structure is not formed of a material that is electrically sensitive to translocation events, and because the support structure is not directly connected to the source and drain circuit. Any passivation or other layers that are provided on top of the channel region material are also not considered in determining the effective length of the nanopore as it relates to sensing of molecules. Only the nanopore extent through the thickness of the channel region material is active in sensing molecules translocating through the nanopore and accordingly only the nanopore extent through the thickness of the channel region material is considered.

The species of interest, against which the nanopore extent is considered, can be a single, complete molecule, or can be one or more molecular components, as given above. The term "molecule" is herein meant to refer to a complete molecular entity, such as a DNA strand. The term "molecular component" is herein meant to refer to a subunit, or component, of a molecule. For example, a nucleotide is a molecular subunit of a DNA molecule. Each of the four DNA bases form four distinct nucleotide types. Molecular components can be, in one example, sequential, individual, distinct entities that together form a molecule.

In accordance with the invention, the nanopore extent through the thickness of the channel region material is selected based on a molecule or one or more molecular components of interest. If it is desired to distinguish between sequential translocation events of molecular components that are coupled in series along a molecular length, as in the case of DNA nucleotides, then the nanopore extent through the channel region material is set based on the length, or extent, of a single nucleotide of interest or a plurality of nucleotides of interest. Alternatively, if it is desired to distinguish between sequential translocation events of complete molecules, such as polymers, then the nanopore extent through the channel region material is set based on the length, or extent, of a complete polymer. The extent of the nanopore through the thickness of the channel region material is therefore selected based specifically on the entity of interest, which may be a complete molecule, a component or components of a molecule, or other molecular subunit or fraction. For clarity of discussion the term "molecule" is frequently used herein with regard to the entity to be sensed, but it is to be recognized that when used in this manner, the term "molecule" is meant to be inclusive of molecular components, fractions, and other molecular subunits.

In one example embodiment, this molecule-specific resolution that is achieved by tailoring the nanopore extent based on the extent of a given molecule, e.g., to thereby enable the ability to determine the sequence of a nucleic acid molecule translocating through the nanopore based on, e.g., the differing electric charge or dipole moments of each of the nucleic acid bases. With the channel region material set to be no thicker than the distance between adjacent bases in a selected strand, e.g., dsDNA, it can be guaranteed that only a single base translocates through the nanopore at a given time, i.e., substantially only one base is present in the nanopore at a given time. As a result, a change in the FET conductance or capacitance can be directly attributable to and is distinctly representative of a specific, single DNA nucleotide. The thickness-controlled nanopore thereby imposes a high degree of spatial resolution on the molecular sensing capability of the FET device, and is particularly well-suited to enable discrimination between each of the different bases of DNA or RNA. Further, as explained in detail below, a binding partner, e.g., a nucleic acid, a small molecule, a protein, or other selected species can be immobilized relative to the nanopore to assist in the identification of a molecule by, e.g., the chemical or electrical interaction between the binding partner and a single molecule or molecular component that is in the nanopore during a given translocation event.

A first example and most preferable channel material provided by the invention and that can achieve a channel region thickness commensurate with nanoscale molecular components is graphene. The term "graphene" is here intended to refer to a single layer or flake of graphite as well as to few-layer graphene or other such layered graphitic structure. In accordance with the invention, one or more layers of graphene can be employed as a channel material. Specifically, one layer, or more than one layer, e.g., 3 layers, 5 layers, 10 layers, or even 100 layers, of graphene can be employed. In single layer form, graphene is a single plane of graphite having $sp^2$ C—C bonds arranged in a honey-comb lattice as an ideal two-dimensional crystal. Few-layer graphene or multi-layer graphene includes several such layers of graphitic bonds.

The thickness of graphene, specifically as a single layer of graphite, is about 3.4 Å, which is comparable to the distance between adjacent nucleotide bases in dsDNA and is smaller than that in ssDNA. Thus, in a graphene-based nanopore FET device provided by the invention, the extent of the nanopore through the graphene channel region is less than the base-to-base distance in ssDNA. As a result, in operation of a graphene-based FET device of the invention to analyze a sequence of DNA, at any time it is guaranteed that only a single DNA base is present in the nanopore of the channel during a translocation event. The graphene-based FET nanopore device of the invention therefore provides particularly high spatial resolution that enables single-base sensing resolution in gene sequencing and that in general is well-suited for high-resolution molecular and analyte sensing applications.

Accordingly, the number of graphene layers forming the channel region is selected to produce a channel region thickness, having a nanopore there-through of that thickness, which corresponds to a selected molecule or molecular component to be sensed. As just explained, a single-layer graphene channel region is of a thickness that is particularly well-suited for DNA and RNA nucleotide sensing and sequencing. A single-layer or multi-layer graphene channel region can be of a thickness that is less than the extent of a selected molecular or molecular component, can be about the same as the extent of a selected molecule or molecular component, or can be slightly greater than the extent of a selected molecule or molecular component, to enable single-molecule or single-molecular component spatial resolution and discrimination. Alternatively, for applications in which single-molecule or single-molecular component resolution is not absolutely required, the number of graphene layers, and corresponding thickness of the graphene channel region, is selected so that no more than a selected number of molecules or molecular components translocate through the nanopore at a given time. For example, the channel region thickness can be selected such that no more than 2, 3, 5, 10, or other selected number of molecules or molecular components are together in the nanopore at a given time during a given translocation event.

Considering other aspects of graphene, electronic transport studies have demonstrated that at room temperature the electronic carrier mobility of graphene can be as high as 60,000 $cm^2$/Vs. The very high electrical mobility in graphene enables a large signal amplitude corresponding to electrical characteristics of a single molecule, e.g., for the charge or dipoles on a DNA strand, and enables operation in the ballistic region. The sensitivity of a graphene-based FET device provided by the invention therefore can far surpass that of devices including conventional microelectronic materials. For some applications, it therefore can be preferable to enable discrimination of individual molecules or molecular components by employing a nanopore FET device of the invention that is implemented with a graphene channel region.

In the fabrication of a graphene-based FET molecular sensor in accordance with the invention, graphene is provided on a support structure or other structure for the FET platform by any suitable method. It is recognized that currently there exist only a limited number of techniques for providing graphene at a selected location. The invention is not limited to a specific technique and contemplates the formation of graphene at a selected site in situ at that site or alternatively, transfer of graphene to a selected site. The invention specifically contemplates the use of advanced techniques in the synthesis of graphene that are not now available. Whatever technique is employed, all that is required is the provision of a graphene channel region or portion of a channel region at or near to a nanopore for sensing translocation events through the nanopore by changes in the graphene conductance.

In one currently-available graphene formation technique, in a first step, a thin piece of commercially-available highly-oriented pyrolytic graphite or a graphite flake is attached to adhesive tape, with the tape folded over the graphite. The tape is then peeled apart to cleave or exfoliate the graphite. This process is repeated a number of times, e.g., 10 times, on the increasingly thinner material, until the material is almost invisible or invisible. Bulk graphite or graphite flakes can also first be suitably attached to, e.g., wet photoresist, provided on a substrate; after baking the resist, the graphite is attached to the resist and using adhesive tape, flakes of graphite can be repeatedly peeled from the bulk. Once graphite flakes, few-layer graphene, or graphene is thusly produced, such is applied to the surface of a structure that is to be employed as the support structure 28 as in the FET device of the example of FIG. 1.

For many applications, it can be preferred to configure the support structure in the vicinity of the nanopore as a relatively thin region in order to minimize the thickness of the nanopore extent beyond the channel thickness. For many applications, a self-supported membrane, such as a micro-fabricated membrane commonly employed in MEMS structures, can be particularly well-suited as a support structure in the vicinity of the nanopore. The term "membrane" is here meant to refer to a relatively thin layer that is supported at its edges. The invention is not limited to a membrane support structure, however. The support structure can be a substrate, wafer, chip, slab, sheet, or other bulk structure, and if desired, can be thinned to provide a trench or other thinned region in the vicinity of a nanopore. It is to be recognized that a wide range of support structures are applicable for the FET nanopore device sensor of the invention. The support structure can be provided with one or more distinct material layers on the surface on which the channel region material is to be disposed. The channel region material need not be directly adjacent to a support structure surface.

If the graphene material is to be applied from an adhesive tape to the surface of a membrane structure, it can be preferred to first apply the graphene to a relatively thick, well-supported structure, such as a substrate, and then to form a membrane in the substrate under the graphene region at the desired location of the FET channel and nanopore. The direct application by rubbing of graphite or few-layer graphene directly onto the surface of a membrane could rupture the membrane. But if an in situ graphene deposition or transfer process that maintains the mechanical integrity of a membrane is available, such can be employed.

Graphitic films that are thinner than about 50 nm are transparent to visible light but can be identified on a silicon dioxide (oxide) surface through a microscope because of the added optical path length resulting from the graphene thickness that shifts the interference colors typical of oxide when viewed through a microscope. As a result, it can be preferable to employ a support structure that is at least partially formed of oxide. For microscope illumination using 550 nm green light, as is conventional, the contrast of graphene with an underlying oxide layer is at its peak for an oxide layer thickness of about 90 nm-100 nm and for an oxide layer thickness of about 270 nm-290 nm. It can therefore be preferred in accordance with the invention to employ a FET support structure having an oxide layer thickness of within one of these ranges. Such is not required, however, if the graphene is visible on a surface of interest.

Figure 3A:
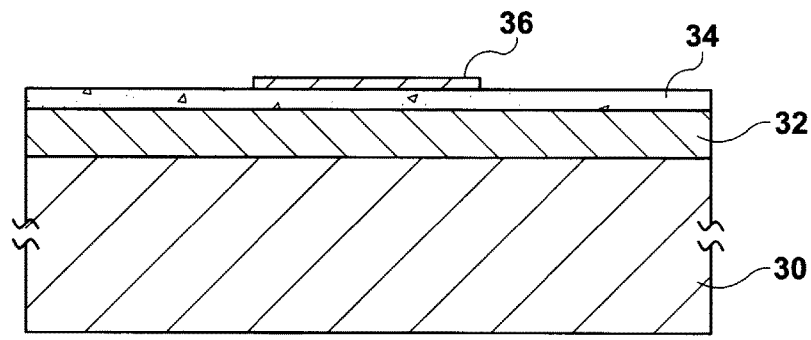
FIGS. 3A-3F are schematic views of microfabrication process steps in an example process sequence provided by the invention for production of the molecular sensor of FIG. 1.

With these considerations, and now referring to FIG. 3A, in the first step of an example fabrication sequence to form a graphene-based FET sensing device in accordance with the invention, there is provided a substrate 30, e.g., a double-sided polished silicon wafer, having on its surface a selected material or materials, e.g., a layer 32 of low stress silicon nitride, $SiN_x$, and/or a layer 34 of silicon dioxide atop the nitride layer 32. In a first example alternative, the lower layer 32 is $SiN_x$ and the upper layer 34 is oxide. In a second example alternative, the lower layer 32 is oxide and the upper layer 34 is $SiN_x$. For clarity the thicknesses shown in FIG. 3 are not to scale. The nitride and/or oxide layers are employed in subsequent steps to form a thinned support structure region in the vicinity of the FET channel region and nanopore location. The layered wafer structure can be cleaned by, e.g., oxygen plasma, if desired to render the top surface hydrophilic, or can otherwise be processed to provide a desired surface condition.

A layer of graphene is then formed on or applied to the top surface of the upper layer, e.g., the oxide layer 34. To apply graphene, e.g., from an adhesive tape, the tape having graphene adhered to it is carefully pressed onto the upper surface 34. The tape is then removed, e.g., by dissolving, and the structure washed by solvent, e.g., acetone and IPA. In this way, a region of graphene 36 few-layer graphene, or other graphitic layered region is transferred onto the surface of the upper layer 34. The graphene can alternatively be deposited on the surface, formed in situ on the surface, or transferred to the surface by an alternative technique.

The layers 32, 34 provided on the Si substrate are selected in part to enable visualization of a region of graphene disposed on the substrate. Because the refraction of $SiN_x$ is about 2, which satisfies the extinction condition on a Si substrate, the maximum contrast between graphene and nitride occurs at zero reflectivity, whereby graphene is invisible on a nitride layer disposed directly on a Si substrate. But if a layer of oxide is provided between the nitride layer and the substrate, graphene is visible on a nitride layer. Therefore, if the upper layer 34 is provided as nitride and the lower layer 32 is provided as oxide, the graphene can be visualized on the nitride surface. If the lack of graphene visibility on nitride or other selected material can be alleviated, then the oxide layer can be omitted between the nitride layer and the substrate. Alternatively, the layer of $SiN_x$ can be omitted and only a layer 34 of oxide employed for forming a support structure, or the upper layer can be formed of oxide and the lower layer formed of nitride. It is recognized that $SiN_x$ can be particularly well-suited for many applications due to its robust mechanical properties.

The invention is not limited to a particular support structure material or combination of materials, however. All that is required is a surface on which the presence of graphene can be identified and located. Thus, whatever surface layers are employed, once the graphene is transferred to the surface of the layers, then using optical microscopy, scanning electron microscopy, or other selected technique, regions of graphene are identified and located on the surface for formation of the FET device at that location. Atomic force microscopy can be further employed to identify regions of graphene and measure the thickness of the graphene.

Figure 3B:
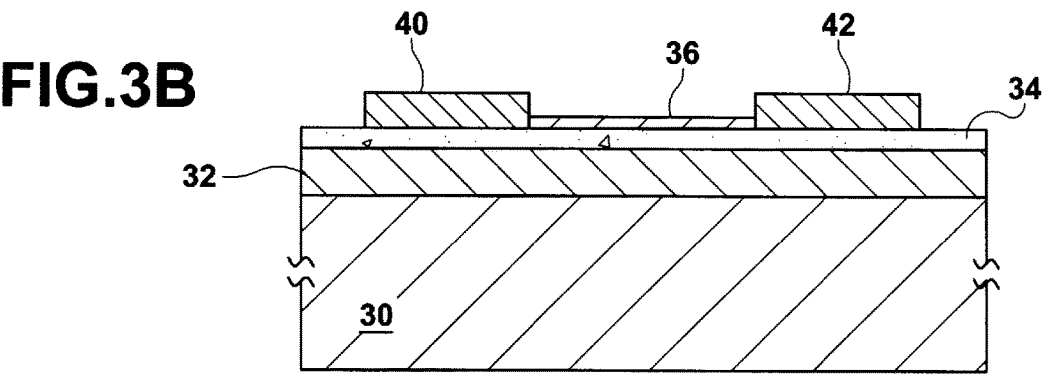

Referring to FIG. 3B, source and drain regions 40, 42, are then formed in contact with a selected graphene region 36 by, e.g., electron beam lithography, or other suitable process. The length of the graphene channel is preferably between about 1 µm-2 µm or less, and preferably can be in the nanometer range. To achieve a desired channel length, the source and drain regions are formed at a location around a graphene region having the corresponding extent, or alternatively, a graphene region is first patterned and etched, in the manner described below, to provide the desired channel length. The source and drain regions are formed of a selected electrically conducting or semiconducting material, e.g., a metal such as Ni, Ti/Pd, Pt, or other selected metal, or semiconducting material, such as polysilicon, silicon, or electrically conducting polymer. Vapor processes can be employed in the conventional manner to form the source and drain regions. For example, thermal evaporation or other suitable process can be employed for metal deposition. The sequence step of source and drain region formation can also be employed to form contact, or bond, pads and connections from the source and drain regions to those bond pads, in the conventional manner for external electrical circuit connection to the source and drain.

Figure 3C:
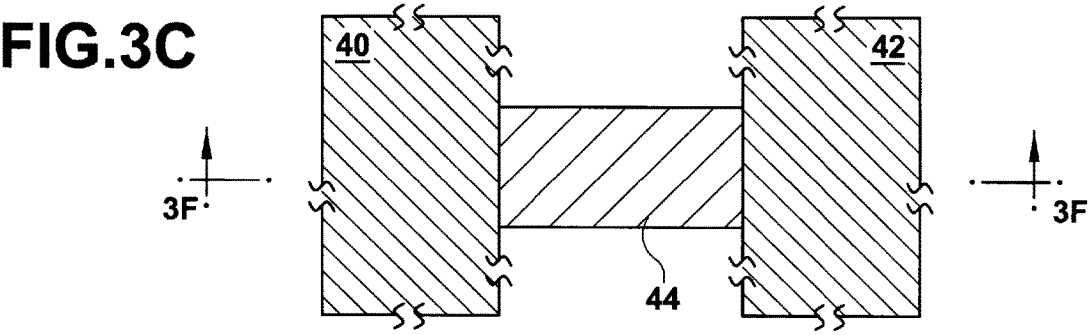

Referring to FIG. 3C, in a next process step, the graphene region can be patterned and etched, if desired, to remove excess graphene such that a selected graphene channel geometry between the source and drain regions is produced. For many applications, a generally rectangular ribbon-shaped or strip-shaped graphene channel region 44 can be preferred. Such is not required, however, and any suitable channel geometry can be employed. A graphene channel width that is less than about 1 µm can be preferred for many applications, and a graphene channel width in the nanometer range is more preferably provided, e.g., between about 10 nm-25 nm. Photolithography with negative photoresist and oxygen plasma etching, or other selected etching process, can be employed to pattern and etch a graphene region to produce the selected graphene channel geometry. It can be preferred to record the position of the graphene channel at this process step so that the location of the device can be identified at subsequent back-side process steps.

Figure 3D:
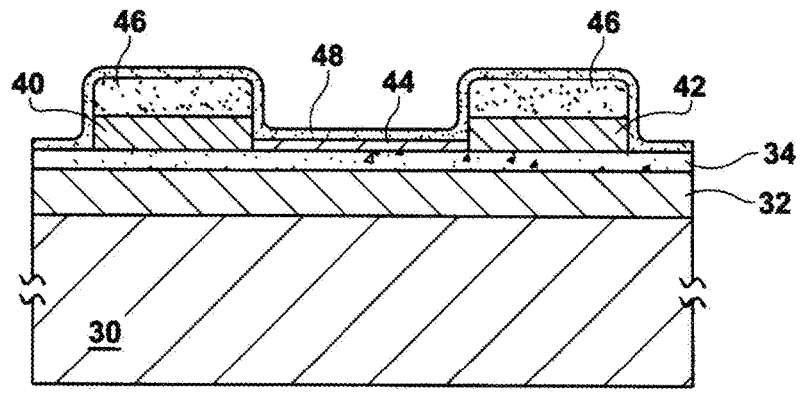

Referring to FIG. 3D, a first electrically insulating layer 46 optionally can be provided over the source and drain regions 40, 42, and a second insulating layer 48 can optionally be provided over the entire device, including the graphene channel 44, to reduce the impact of the operating environment on the operational sensing characteristics of the device. Both insulating layers can be provided as $SiN_x$, e.g., PECVD $SiN_x$, as an oxide, as a polymer, or other selected insulating material. The first insulating layer 46 can be provided with a thickness of, e.g., about 50 nm-60 nm and the second insulating layer 48 can be provided with a thickness of, e.g., about 20 nm.

Figure 3E:
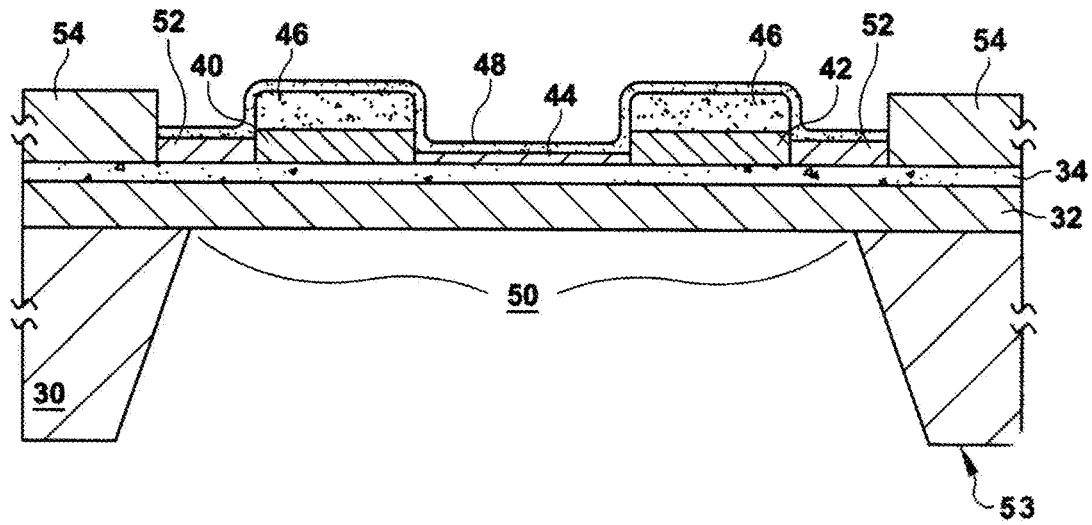

At this point in the process it is convenient to tailor the thickness of the support structure in the vicinity of the FET channel region and the intended nanopore position. Referring to FIG. 3E, in one well-suited technique, the substrate 30 is bulk-etched to form a membrane 50 on which are supported the source and drain regions 40, 42, and the channel region 44. For clarity, FIGS. 3A, 3B, and 3D-3E do not depict the existence of nitride and oxide layers 32, 34 on the backside 53 of the substrate. In practice, the first steps of forming layers 32, 34 on the surface of the substrate also result in the formation of those layers on the backside of the substrate. In the formation of a membrane, then, any such oxide and nitride layers, as well as the silicon bulk, are removed.

In one example process, both sides of the substrate are coated with a protective layer, e.g., PMMA, in a thickness of, e.g., 250 nm-300 nm. Electron beam lithography is then carried out on the backside of the wafer at the position opposite the graphene FET device to pattern a square or other selected membrane shape. For many applications, a membrane having dimensions of, e.g., 80 µm×80 µm, or 100 µm×100 µm, can be employed. After development of the PMMA or other protective layer, any oxide and nitride layers on the back side of the wafer are then removed, e.g., with BOE HF and nitride etchants. At this point, the silicon wafer can then be bulk etched to form the membrane. The bulk etching can be carried out by any convenient method, e.g., by plasma etching or other vapor etching, e.g., with $XeF_2$, by wet etching, such as with KOH, or with other suitable etching with sufficient selectivity of silicon over nitride, oxide or other surface layer at which the etch will end. Then one or more of the surface layers can be removed, if desired, to form a membrane of a thinner extent. For example, an underlying oxide layer can be removed to produce a nitride membrane.

This results in a self-supported membrane 50 that is supported at its edges by the substrate 30. The FET device is positioned on the membrane. In FIG. 3E there are shown connections 52 between the source and drain regions 40, 42 to corresponding bond pads 54 that are off the membrane. These connections and bond pads are formed at the time of source and drain region formation as described above. Thus, a portion of the FET device elements and circuitry can be disposed on the membrane with other of the elements disposed on the substrate at locations distant from the membrane. There is not specific requirement for the location of the device elements on or off the membrane. All that is required is a relatively thin support region at the location intended for the nanopore of the FET device. Indeed, many FET devices can be provided on the membrane, with connections from each FET device to bond pads at the exterior periphery of the membrane. A 100 µm×100 µm membrane can be formed with 20 or more FET devices on the membrane to accommodate simultaneous and parallel molecular sensing, as described below.

It is now clear from FIG. 3E that the thickness of the surface layer or layers 32, 34 sets the thickness of the membrane. These layers are therefore preferably tailored in thickness at the time of their deposition to set the desired membrane thickness and correspondingly, to set the length of the nanopore section that traverses the membrane. For many applications, it can be preferred to select an oxide layer thickness that enables visualization of graphene and then to set a nitride layer thickness, if employed, to provide adequate mechanical support while also accommodating a selected nanopore formation process. In general, a relatively thinner membrane is preferred because the membrane thickness directly affects the voltage required for translocation.

Alternatively, commercially-available membranes can be employed, e.g., $SiN_x$ TEM grid membranes having a thickness of, e.g., about 30 nm, can be employed. As explained previously, if it is not possible to position a graphene layer or layers on a membrane, including a commercial membrane, without harming the membrane, then the process described above, in which graphene is formed on a structure and then the structure thinned to form a membrane, can be preferred. Further, the invention is not limited to membrane structures for the geometry of a support in the vicinity of the FET channel. Plates, cantilevers, bridges, trusses, substrates, or other suitable configuration can be employed for the support at the location of the FET channel.

Figure 3F:
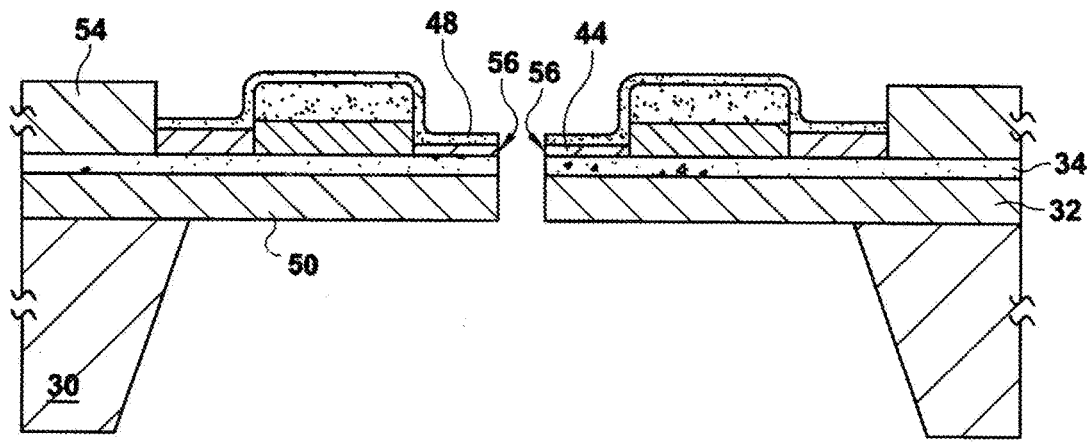

Turning now to FIG. 3F, at this point, a nanopore is formed at a selected location relative to the graphene channel region. Note that the cross sectional view of FIG. 3F is taken at the cross section shown in the planar view of FIG. 3C. In accordance with the invention, the nanopore is provided with an extent corresponding to a molecule, molecular component, or other species of interest. For a wide range of molecular sensing applications, it is preferred that the nanopore be less than 1000 nm in diameter, preferably less than 100 nm. For many applications, a nanopore diameter less than about 10 nm or less than about 5 nm is preferred, with a diameter of between about 1.5 nm and about 2 nm preferred for ssDNA sensing. The invention is not limited to a particular nanopore diameter and instead requires that the diameter provide adequate extent for a molecule or other species of interest. When the nanopore diameter is comparable to the extent of a molecular component, e.g., a DNA base, any geometric differences between bases can result in differing translocation duration, aiding in circuit parameter analysis for discrimination of specific DNA bases.

In one example process for producing the nanopore, the whole substrate arrangement is loaded into a TEM specimen chamber and the graphene FET device is located and identified under the TEM. Then a high energy electron beam is focused into a 1-2 nm beam spot at the desired location of the nanopore, e.g., at a point centrally along the graphene channel region, at the edge of the channel region, or just adjacent to the channel region, and a nanometer-sized hole is punched through the graphene layer and the underlying oxide/$SiN_x$ membrane. It is preferred to direct the electron beam to the backside of the membrane 50 in formation of the nanopore. This eliminates exposure of the insulating layers 46, 48, to the electron beam and the unwanted electrical charging of those layers that could result. With, e.g., a JOEL 2010F TEM, using a spot size 1, convergent angle 3, beam of 25-35 $pA/cm^2$, and 300-500K×, a nanopore of a selected diameter can be formed through the membranes in a matter of seconds to minutes. As can be recognized, the size of the nanopore can be controlled by choice of the condenser aperture, illumination time, and other beam characteristics. If desired and/or required, the FET device can be annealed after the nanopore formation to improve electrical characteristics of the device and in particular the channel region. The high-energy electron beam can introduce a potential barrier around the nanopore and therefore decrease the channel region conductance. Thus, an optional thermal anneal can be performed to improve the conductance of the channel region.

With this step, a functional graphene-based FET molecular sensor is completed and ready for connection in a circuit and an environment of molecules or other species to be sensed. Note in FIG. 3F that in the final device configuration, the channel region 44 of the FET device is sandwiched between the membrane surface layer 34, e.g., nitride, and an upper insulating layer 48. As a result, neither the top surface nor the bottom surface of the channel region makes any substantial physical contact with molecules to be sensed or the environment in which the molecules are provided. The channel region 44 is exposed to a molecule or molecular component and the molecular environment only at the edge 56 of the nanopore. This nanopore edge 56 is shown in side-view cross section in FIG. 3F and is shown in perspective view in FIG. 1. Molecule-channel interaction can therefore take place only along the extent of the walls of the nanopore, through the thickness of the channel, e.g., through the thickness of a graphene layer. With this arrangement, it is guaranteed that the zone of molecular sensing is constrained to the extent of the nanopore through the channel region material, and therefore that the channel region layer thickness can indeed set the spatial extent of molecular interaction with the FET sensor. Single-molecule or single-molecular component sensing or other selected limited molecular sensing accordingly can be enforced.

In accordance with the invention, the nanopore walls, i.e., the cross-sectional nanopore edge 56, can be provided on its surface with reaction entities or other species, e.g., binding partners, that are specific for a moiety of interest to be sensed, or reacted with. The nanopore periphery through the thickness of the channel region can be functionalized with a selected species. Such functionalization results in FET behavior that is indicative of reaction between the functionalization species and a corresponding moiety or interest present in the environment of molecules to be sensed. Provision of a functionalization species at the nanopore can be carried out in the manner described in U.S. Patent Application Publication US2002/0117659, published Aug. 29, 2002, the entirety of which is hereby incorporated by reference.

Although the fabrication process described above was specified for the particular channel region material graphene or multiple layers of graphene, the invention is not limited to such. The channel region material layer can be formed of any suitable material, layers of material, or composite layers of multiple materials, that meets the requirement of conductance as an FET channel, that can be etched to form a nanopore there-through, and that can be provided in a thickness corresponding to a selected molecule or molecular component to be sensed. Silicon, polysilicon, or other II-VI material, III-V materials, conductive polymers, and other microelectronic materials can be employed as channel materials. Such can be provided by, e.g., SOI wafers, by epitaxial deposition or other vapor formation process, by evaporation, sputtering, CVD or other suitable process that enables the formation of a selected channel region material. Once deposited, the channel region material can be thinned to the desired thickness corresponding to a molecule to be sensed, such that single or near-single molecule sensing resolution is attained.

Figure 4:
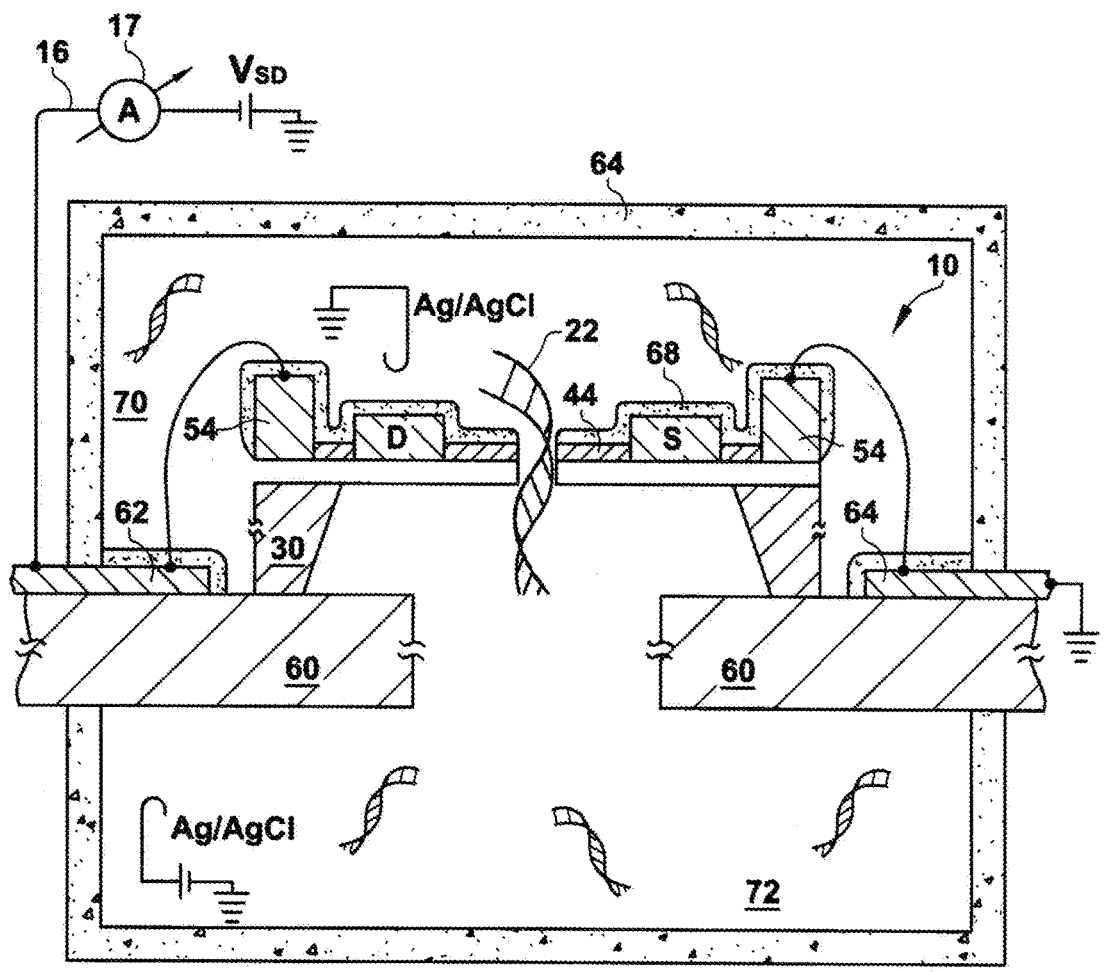
FIG. 4 is a schematic perspective view of the molecular sensor of FIG. 1 configured for operation in a sensing environment.

Whatever channel region material is employed, once the nanopore FET device fabrication is complete, the device is arranged for molecular sensing in a selected environment. Referring to FIG. 4, in one example configuration, the molecular sensing device 10 is bonded to, e.g., a PCB chip carrier 60. The source and drain contact pads 54 are connected to connector pads 62, 64 by conventional wire bonding or other suitable technique. Preferably all bonding wires and contact pads are passivated with, e.g., $SiN_x$ or $HfO_2$, in the manner described above or with another passivation layer 68. The device 10 and chip carrier 60 are enclosed in a chamber, e.g., a PDMS chamber 64 which forms with the front side of the device a supply reservoir 70 for supplying a solution of interest to be analyzed, and which forms with the back side of the device a collection reservoir 72 for collecting a solution after it has been analyzed. These reservoir functions can be reversed if desired. The sealed mating of the substrate 30 with the circuit board 60 enables separating of the chamber into the two reservoirs. Alternative reservoir configurations can be employed as-suited for a given application. The reservoirs can be provided as vessels, as flow channels, or as other structures for guiding a fluid having molecular species toward the nanopore.

Molecules of interest, e.g., DNA strands 22, are provided in the solution to be analyzed by translocation through the nanopore. Other example molecules to be analyzed include, in general, biomolecules, such as ssDNA, dsDNA or RNA strands, oligonucleotides, or nucleic acids in general, such as proteins, and other biomolecules. Non-biological molecules, and indeed, any non-molecular species can also be analyzed as-desired, if such can be supplied for translocation through the nanopore.

In accordance with the invention, a driving force is imposed across the nanopore between the two reservoir solutions, to cause translocation of species in the supply reservoir through the nanopore and into the collection reservoir. In one convenient configuration, Ag/AgCl electrodes, or other electrodes, can be used to apply a voltage difference across the nanopore. Alternatively, gate electrodes defined on the chip carrier can be used to apply solution potentials. No particular driving force is required by the invention; the translocation of species through the nanopore for analysis is all that is required. In operation, it can be preferably to rinse the reservoirs with ethanol and DI water before introduction of a solution of interest. Further, it can be preferred to operate the system inside, e.g., a Faraday box to eliminate external noise.

As shown in FIG. 4, in the FET circuit 16 there is provided a source-drain bias voltage source, $V_{SD}$, and at least one circuit parameter measurement device, e.g., a current amplifier 17. When a potential difference is applied between the two solution reservoirs 70, 72, an electric field is established across the nanopore that drives an electrically charged solution through the nanopore by electrophoresis. As explained above, molecules in the solution, e.g., a DNA strand 22, translocate through the nanopore as a result of the driving force between the reservoirs. The charge and dipoles of the DNA or other molecules or molecular components cause a change in conductance of the channel region 44 that is directly attributable to the one or more molecules or molecular components in the nanopore at a given time. As explained above, with selection of the thickness of the channel region material, as few as one molecule or molecular component can be singly and controllably translocated through the nanopore. The FET circuit parameters correspondingly change as a result of the conductance change due to molecular translocation, and are sensed by the current amplifier or other device or system.

Figure 5:
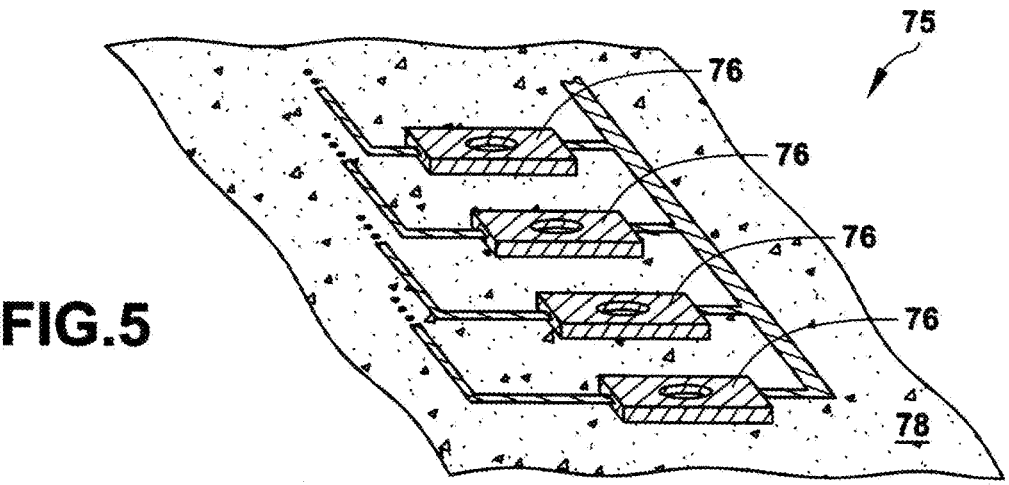
FIG. 5 is a schematic perspective view of a series of parallel molecular sensors provided by the invention for simultaneous parallel molecular sensing.

As explained above, multiple FET devices can be fabricated on a single support substrate, e.g., on a membrane. This configuration enables parallel, simultaneous sensing operations by multiple FET devices provided in communication with a common reservoir. For example, as shown in FIG. 5, there can be provided a molecular sensing array 75 of FET devices configured on a support structure 78 for parallel molecular analysis of a sample solution. Each device 76 in the array 75 can be configured to operate for translocation of molecules through a nanopore in the channel region or adjacent to the channel region of the device.

With the above discussion, it is demonstrated that the FET molecular sensor of the invention enables superior resolution and sensitivity for the detection and analysis of molecules and molecular components. The resolution of the detection can be made as low as a single DNA base by employing an FET channel region material having a thickness that corresponds to the extent of a DNA base. Graphene is therefore particularly well-suited as a channel region material. The superior electrical characteristics of graphene, along with its inherent thinness, enable a graphene nanopore FET sensor to achieve molecular sensing, and gene sequencing, at very high resolution and sensitivity.

It is recognized, of course, that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. A molecular sensor comprising:
    a solid state and electrically conducting sensing material including a sensing aperture extending through a thickness of the sensing material;
    a continuous, electrically conducting path extending in the sensing material around the sensing aperture, the continuous electrically conducting path in the sensing material extending from an electrically conducting source region at a first end of the electrically conducting sensing material to an electrically conducting drain region at a second end of the electrically conducting sensing material;
    a supply reservoir connected to provide a molecular species from the supply reservoir to an input port of the sensing aperture, the molecular species in the supply reservoir having a molecular length;
    a collection reservoir connected to collect the molecular species from an output port of the sensing aperture after translocation of the molecular species from the supply reservoir through the sensing aperture;
    the sensing aperture having a length between the input port and the output port, through the thickness of the sensing material, that is substantially no greater than a distance between adjacent bases in ssDNA; and
    an electrical connection to the continuous electrically conducting path in the sensing material through each of the electrically conducting source region and the electrical conducting drain region, to measure a change in an electrical characteristic of the sensing material during the molecular species translocation through the sensing aperture.

2. The molecular sensor of claim 1 wherein the molecular species in the supply reservoir includes a series of molecular components that are coupled along the molecular length.

3. The molecular sensor of claim 1 wherein the molecular species in the supply reservoir comprises a biomolecule.

4. The molecular sensor of claim 1 wherein the molecular species in the supply reservoir comprises a polymer molecule.

5. The molecular sensor of claim 1 wherein the molecular species in the supply reservoir comprises a nucleic acid molecule.

6. The molecular sensor of claim 5, wherein the nucleic acid molecule in the supply reservoir comprises a DNA strand.

7. The molecular sensor of claim 6 wherein the DNA strand includes a series of bases coupled along the DNA strand, and wherein the sensing aperture length allows only one base to be present in the sensing aperture at a given time.

8. The molecular sensor of claim 5 wherein the nucleic acid molecule in the supply reservoir comprises a RNA strand.

9. The molecular sensor of claim 5 wherein the nucleic acid molecule in the supply reservoir includes a series of nucleotides that are coupled along the nucleic acid molecular length.

10. The molecular sensor of claim 1 wherein the sensing aperture comprises a nanopore having a diameter no greater than about 10 nm.

11. The molecular sensor of claim 1 wherein the sensing aperture comprises a nanopore having a diameter no greater than about 5 nm.

12. The molecular sensor of claim 1 further comprising an electrical circuit connected to the electrical connection to measure a change in electrical conductance of the sensing material during molecular species translocation.

13. The molecular sensor of claim 1 wherein the electrical connection to the sensing material comprises an electrical connection to the electrically conducting source region and to the electrically conducting drain region.

14. The molecular sensor of claim 13 further comprising an electrical circuit including a current amplifier connected between the source and drain regions.

15. The molecular sensor of claim 1 wherein the sensing material has a sensing material length between the electrically conducting source region and the electrically conducting drain region that is less than about 2 microns.

16. The molecular sensor of claim 1 wherein the sensing material has a sensing material width that is less than about 1 micron.

17. The molecular sensor of claim 1 wherein the sensing aperture comprises aperture walls extending through the thickness of the sensing material, along the sensing aperture length, the aperture wall surface being uncoated and exposed.

18. The molecular sensor of claim 1 wherein the electrically conducting sensing material, the electrically conducting source region, and the electrically conducting drain region are all disposed on a common surface of a support structure, the support structure including a support structure aperture that is aligned in communication with the sensing aperture.

19. The molecular sensor of claim 18 wherein the support structure comprises $SiN_x$.

20. The molecular sensor of claim 18 wherein the support structure is electrically insulating.

* * * * *